United States Patent
Guo et al.

(10) Patent No.: US 6,492,320 B2
(45) Date of Patent: Dec. 10, 2002

(54) MULTIFUNCTIONAL, GRANULATED PELLET AID AND PROCESS

(75) Inventors: Hailan Guo, Warrington, PA (US); Wen H. Chia, Ambler, PA (US); Curtis Schwartz, Ambler, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/749,196

(22) Filed: Dec. 27, 2000

(65) Prior Publication Data

US 2002/0086809 A1 Jul. 4, 2002

Related U.S. Application Data

(63) Continuation-in-part of application No. 09/667,646, filed on Sep. 22, 2000.
(60) Provisional application No. 60/156,080, filed on Sep. 24, 1999.

(51) Int. Cl.$^7$ .......................... C11D 3/37; C11D 11/02; C11D 17/00
(52) U.S. Cl. .................. 510/446; 510/224; 510/349; 510/361; 510/441; 510/443; 510/444; 510/446; 510/452; 510/477; 510/533
(58) Field of Search ................. 510/224, 349, 510/361, 441, 443, 444, 446, 452, 477, 533

(56) References Cited

U.S. PATENT DOCUMENTS

| | | | |
|---|---|---|---|
| 3,827,996 A | * 8/1974 | Bereniewicz | 260/29.6 |
| 4,456,726 A | 6/1984 | Siol et al. | 524/501 |
| 4,539,361 A | 9/1985 | Siol et al. | 524/458 |
| 4,916,171 A | 4/1990 | Brown et al. | 523/161 |
| 4,921,898 A | * 5/1990 | Lenney et al. | 524/459 |
| 5,340,858 A | 8/1994 | Bauer et al. | 524/162 |
| 5,350,787 A | 9/1994 | Aydin et al. | 524/162 |
| 5,352,720 A | 10/1994 | Aydin et al. | 524/162 |
| 5,360,567 A | 11/1994 | Fry et al. | 252/90 |
| 5,521,266 A | 5/1996 | Lau | 526/200 |
| 5,656,584 A | * 8/1997 | Angell et al. | 510/441 |
| 5,883,061 A | * 3/1999 | Duccini et al. | 510/224 |
| 5,916,866 A | 6/1999 | Davies et al. | 510/441 |
| 5,922,661 A | * 7/1999 | Duccini et al. | 510/224 |
| 6,114,289 A | * 9/2000 | Capeci et al. | 510/108 |

FOREIGN PATENT DOCUMENTS

| | | |
|---|---|---|
| EP | 0 576 128 A1 | 12/1993 |
| EP | 711828 A2 * | 5/1996 |
| EP | 716144 A2 * | 6/1996 |
| EP | 896 052 A1 | 2/1999 |
| EP | 972825 A2 * | 1/2000 |
| EP | 1087009 A * | 3/2001 |
| GB | 983243 * | 2/1965 |
| GB | 989683 * | 4/1965 |

* cited by examiner

*Primary Examiner*—Mark Kopec
*Assistant Examiner*—Brian P. Mruk
(74) *Attorney, Agent, or Firm*—Stephen E. Johnson

(57) ABSTRACT

The present invention relates to a multifunctional pellet aid including one or more binders, wherein at least one binder is an acrylic based polymer having a Tg ranging from −20° C. to +95° C., one or more inorganic solids and one or more organic solids; the particle size of the pellet aid ranging from 100 μm to 3000 μm. Adding 0.25 to 10% by weight of the multifunctional pellet aid, based on the total weight of the pellet, to a plurality of ingredients and compacting the pellet aid and ingredients to form a pellet, affords a pellet having improved mechanical strength as a solid and rapidly disintegrating upon contact with an aqueous system.

20 Claims, No Drawings

MULTIFUNCTIONAL, GRANULATED PELLET AID AND PROCESS

The present application is a continuation-in-part of U.S. patent application Ser. No. 09/667,646, filed Sep. 22, 2000, which claims priority to U. S. Provisional Application Ser. No. 60/156,080, filed September 24, 1999.

The present invention relates to pellets which disintegrate rapidly in aqueous media and which have sufficient mechanical strength to withstand breakage during manufacture, storage, shipping and handling. More particularly, the invention is directed to multifunctional aids for preparing pellets.

The term "pellet" refers to any solid formulation, including but not limited to, tablets, bricks, briquettes, bars, granules, granulates, co-granulates, balls, or blocks. Pellets are well known in the fields of medicine, food science, agriculture, consumer products and more recently they are being used in detergent applications. Pellets offer certain advantages over granular compositions. Pellets are non-dusting, do not require measuring, take up less space because they are compressed and the ingredients that make up a pellet do not separate during transit and storage. Pellets also allow the separation of incompatible ingredients within different layers of the pellet body. Pellets are generally made by compressing or compacting a solid composition which includes one or more active components and various additives or ingredients.

An ongoing problem associated with pellets is the difficulty in providing pellets which have adequate mechanical strength when compacted, yet disintegrate and dissolve quickly when added to an aqueous system. One approach has been to use an additive in preparing a pellet. The problem, however, has proved especially difficult due to the relative rates of dissolution or disintegration of pellets currently in use as compared with granular compositions. Often, it is necessary to compromise between the speed of disintegration of the pellet at the time of use and the strength of handling the pellet before use. In the manufacturing process, a balance must be maintained between a pellet compaction pressure which is, on the one hand, high enough to ensure that the pellets are well formed and do not fracture and/or crumble during transport and storage, and a pellet compaction pressure which is, on the other hand, low enough to achieve an appropriate solubility/disintegration profile. A single material or pellet aid that can be added to ingredients that constitute a pellet would be of significant utility, particularly if the pellet aid possessed a variety of useful functions, in other words a multifunctional pellet aid. The term multifunctional in the present invention refers to a granulated, polymeric pelleting aid which functions for example as a binder, a disintegrating agent and a wicking agent in one solid material.

U.S. Pat. No. 5,916,866 discloses a process for making compacted detergent tablets comprising spraying a coating of a water-soluble organic polymer binder onto the exterior of particles of detergent compositions including a detergent actives and detergent builders. European publication EP 0 896 052 A1 discloses detergent tablets with improved handling strength and swift dissolution which comprise a non-gelling binder and a coating. Examples of non-gelling binders are taken from the prior art but suitable coating materials are dicarboxylic acids for example selected from oxalic acid, malonic acid, succinic acid, glutaric acid, adipic acid, pimelic acid, suberic acid, azelaic acid, sebacic acid, undecanedioic acid, dodecanedioic acid, tridecanedioic acid and mixtures thereof U.S. Pat. No. 5,883,061 teaches polymeric tablet binders which comprise (meth)acrylic acid, maleic anhydride, alkyl (meth)acrylates, alkylhydroxy (meth) acrylates or styrene monomers in polymerised form. The polymeric binders have a Tg ranging from +40 to +120° C. and a molecular weight of from 10,000 to 120,000. U.S. Pat. No. 5,360,567 discloses a detergent tablet coated with a polymeric binder, namely polyethylene glycol, which is also capable of acting as a disintegrant by disrupting the structure of the tablet when the tablet is immersed in water. The '567 patent, however, teaches that it is highly advantageous for the binder/disintegrant to coat or envelop the detergent matrix particles rather than to be simply mixed with them. Clearly, alternative pellet aids are still sought, pellet aids which have more than one type of functionality and which provide pellets having improvements in tablet strength and the rate of disintegration in aqueous media. A single, multifunctional material that can aid in the production of a compacted pellet, a pellet which disintegrates rapidly in aqueous media and which has sufficient mechanical strength to withstand breakage during storage, shipping and handling, would be of substantial utility.

The inventors have discovered a granulated, polymeric pelleting aid which surprisingly functions as a binder, a disintegrating agent and a wicking agent in one solid material. The present invention provides novel pellet aids in the form of granulated compositions used in the processing of pellets by direct compression. Pellets processed with such solid compositions have sufficient mechanical strength to be handled and stored without breakage, yet dissolve rapidly upon contact with water. The pellet aid can be incorporated at any stage of the pelleting process prior to pellet compaction and, optionally the pellet aid can be co-granulated with other functional additives.

In a first aspect of the present invention, there is provided a granulated composition as a pellet aid for binding one or more ingredients and then compacted into a pellet, the pellet having sufficient mechanical strength and rapidly disintegrating when contacted with an aqueous system, the composition including: (a) 20 to 80% by weight of one or more binders, wherein at least one binder is a solution, suspension or emulsion polymer having a Tg ranging from −20° C. to +95° C.; (b) 0 to 40% by weight of one or more inorganic solids; and (c) 10 to 80% by weight of one or more organic solids, wherein the granulated composition is present in an amount from 0.25 to 5% by weight of the total weight of the pellet, the granules having a particle size ranging from 100 $\mu$m to 3000 $\mu$m.

In a second aspect of the present invention, there is provided a process for preparing a multifunctional pellet aid which includes the steps of: (a) premixing 0 to 40% by weight of one or more inorganic solids and 10 to 80% by weight of one or more organic solids; (b) spraying 20 to 80% by weight of one or more solution, suspension or emulsion polymers having a Tg ranging from −20° C. to +95° C. on to the premixed solids to achieve a particle size ranging from 100 $\mu$m to 3000 $\mu$m.

In a third aspect of the present invention, there is provided a process for preparing a multifunctional pellet aid which includes the steps of: (a) preparing a slurry of 0 to 40% by weight of one or more inorganic solids and 20 to 80% by weight of one or more solution, suspension or emulsion polymers having a Tg ranging from −20° C. to +95° C.; and (b) spraying the slurry on to 10 to 80% by weight of one or more organic solids to achieve a particle size ranging from 100 $\mu$m to 3000 $\mu$m.

In a fourth aspect of the present invention, there is provided a process for preparing a solid pellet having high mechanical strength, which can withstand storage and handling without fracturing, and which rapidly disintegrates upon contact with an aqueous system comprising the steps of: (a) mixing 90 to 99.75% by weight of a plurality of ingredients and 0.25 to 10% by weight of a granulated, multifunctional pellet aid composition, wherein the pellet aid comprises (i) 20 to 80% by weight of one or more binders, wherein at least one binder is a solution, suspension or emulsion polymer having a Tg ranging from $-20°$ C. to $+95°$ C.; (ii) 0 to 40 % by weight of one or more inorganic solids; and (iii) 10 to 40% by weight of one or more organic solids, the particle size of pellet aid ranging from 100 $\mu$m to 3000 $\mu$m; (b) compacting the mixture of ingredients and pellet aid to form a pellet.

The solid pellet aid composition usefully employed in accordance with the present invention includes one or more polymeric binders, one or more inorganic solids and one or more organic solids. Suitable binders that make up the pelleting aid include for example acrylic based solution, suspension or emulsion polymers; saccharides such as dextrose, glucose, sucrose, maltose, fructose, cyclodextrin and cyclodextrin derivatives; polysaccharides such as starch, starch derivatives, cellulose, cellulose derivatives such as sodium carboxymethylcellulose, cellulose ethers, methyl cellulose, ethyl hydroxyethyl cellulose, cross-linked cellulose derivatives; naturally occurring gums such as tragacanth gum and gum arabic. Suitable inorganic solids that make up the pellet aid include for example zeolites; clays; alkali- or alkaline-earth metal silicates, such as aluminosilicates; silica; alkali- and alkaline-earth metal carbonates, such as sodium carbonate and magnesium carbonate; alkali- and alkaline-earth metal citrates, such as sodium citrate and calcium citrate; alkali- and alkaline-earth metal acetates, such as sodium acetate. Suitable organic solids that make up the pellet aid include for example polymer dispersants such as poly(meth)acrylic; saccharides such as dextrose, glucose, sucrose, maltose, fructose, cyclodextrin and cyclodextrin derivatives; polysaccharides such as starch, starch derivatives, cellulose, cellulose derivatives such as sodium carboxymethylcellulose, cellulose ethers, methyl cellulose, ethyl hydroxyethyl cellulose, cross-linked cellulose derivatives.

The polymers usefully employed in accordance with the present invention may be soluble or insoluble in water; those which are water insoluble are preferably readily dispersible in water. As used herein, the term "water soluble", as applied to monomers, indicates that the monomer has a solubility of at least 1 gram per 100 grams of water, preferably at least 10 grams per 100 grams of water and more preferably at least about 50 grams per 100 grams of water. The term "water insoluble", as applied to monomers, refers to monoethylenically unsaturated monomers which have low or very low water solubility under the conditions of emulsion polymerization, as described in U.S. Pat. No. 5,521,266. An aqueous system refers to any solution containing water.

Suitable solution, suspension or emulsion polymers usefully employed in accordance with the present invention are prepared from one or more of the following monomers: (meth)acrylic acid, (meth) acrylate esters such as methyl (meth)acrylate, ethyl (meth)acrylate, butyl (meth)acrylate iso-butyl (meth)acrylate or t-butyl(meth)acrylate, 2-ethylhexyl (meth) acrylate, decyl (meth)acrylate iso-bornyl (meth)acrylate, and (meth)acrylate esters of alkylene glycols, polyalkylene glycols and ($C_1$–$C_{30}$) alkyl substituted polyalkylene glycols including esters of the formula $CH_2=CR_1—CO—O(CH_2CHR_3O)_m(CH_2CH_2CHR_3O)_nR_2$ where $R_1$=H or methyl; $R_2$=H or $C_1$–$C_{30}$ alkyl; $R_3$=H or $C_1$–$C_{12}$ alkyl, m=O-40, n=O-40, and m+n is $\geq 1$, such as hydroxyethyl (meth)acrylate, hydroxypropyl (meth)acrylate; $C_1$–$C_{30}$ alkyl-substituted acrylamides; vinyl sulfonate, acrylamido propane sulfonate; dimethyl amino propyl (meth)acrylamide, alkyl vinyl ethers, vinyl chloride, vinylidene chloride, N-vinyl pyrollidone, allyl containing monomers; aromatic vinyl compounds such as styrene, substituted styrenes; butadiene; acrylonitrile; monomers containing aceto acetoxy functional groups such as aceto acetoxy ethyl methacrylate; vinyl esters of saturated carboxylic acid, e.g., acetate, propionate, neodecanoate; acid or base containing monomers such as, for example, (meth) acrylic acid, itaconic acid, maleic acid, fumaric acid, N,N-dimethyl amino ethyl methacrylate; or combinations thereof. Additionally, cross-linking and grafting monomers such as 1,4-butyleneglycol methacrylate, trimethylolpropane triacrylate, allyl methacrylate, diallyl phthalate, divinyl benzene, or combinations thereof may be used. As used herein, by "(meth) acrylate" or "(meth)acrylic", we mean either acrylate or methacrylate for "(meth) acrylate" and acrylic or methacrylic for "(meth)acrylic".

The polymers used in the present invention may be made using known techniques, for example, solution, emulsion or suspension polymerization. Alternatively, a multiphase polymer dissolved or dispersed in water may also be used. By "multi-phase" polymer we mean polymer particles with at least one inner phase or "core" phase and at least one outer or "shell" phase. The phases of the polymers are incompatible. By "incompatible" we mean that the inner and the outer phases are distinguishable using techniques known to those skilled in the art. For example, the use of scanning electron microscopy and staining techniques to emphasize differences in the phases is such a technique. The morphological configuration of the phases of the polymers may be for example, core/shell; core/shell particles with shell phases incompletely encapsulating the core; core/shell with a multiplicity of cores; or interpenetrating network particles or phases that contain a multiplicity of hard and soft phases. The first phase may comprise a "soft" polymer with a Tg in the range $-20$ to $+95°$ C., preferably a Tg in the range from $-1$ to $+95°$ C. Such inner phase polymers may comprise polymerized residues of one or more of the following monomers: (meth)acrylic acid, (meth) acrylate esters such as methyl (meth)acrylate, ethyl (meth)acrylate, butyl (meth) acrylate iso-butyl (meth)acrylate or t-butyl(meth)acrylate, 2-30 ethylhexyl (meth) acrylate, decyl (meth)acrylate iso-bornyl (meth)acrylate, hydroxyethyl (meth)acrylate, hydroxypropyl(meth)acrylate; (meth) acrylate esters, for example, where the ester group is a polyalkylene oxide or a $C_1$–$C_{30}$ alkoxyl polyalkylene oxide; $C_1$–$C_{30}$ alkyl substituted acrylamides; vinyl sulfonate, acrylamido propane sulfonate; dimethylamino propyl(meth)acrylamide, alkyl vinyl ethers, vinyl chloride, vinylidene chloride, N-vinylpyrollidone, allyl containing monomers; aromatic vinyl compounds such as styrene, substituted styrenes; butadiene; acrylonitrile; monomers containing aceto acetoxy functional groups such as aceto acetoxy ethyl methacrylate; vinyl esters of saturated carboxylic acid, e.g., acetate; propionate, neodecanoate; acid or base containing monomers such as, for example, (meth)acrylic acid, itaconic acid, maleic acid, fumaric acid, N,N-dimethylamino ethyl methacrylate. Additionally, crosslinking and grafting monomers such as 1,4-butyleneglycol methacrylate, trimethylolpropane triacrylate, allyl methacrylate, diallyl phthalate, divinyl benzene, or combinations thereof may be used.

The outer phase (sometimes regarded as a "shell" if it encapsulates the inner phase), of the multi-phase polymer may comprise either:

i) a polymer with a relatively high Tg value, for example from +40 to 160° C., which makes the outer phase relatively hard. The outer phase may comprise polymerized residues of one or more of the following monomers: (meth)acrylic acid, (meth) acrylate esters such as methyl (meth)acrylate, ethyl (meth)acrylate, butyl (meth)acrylate iso-butyl (meth)acrylate or t-butyl(meth)acrylate, 2-ethylhexyl (meth) acrylate, decyl (meth)acrylate isobornyl (meth)acrylate, hydroxyethyl (meth)acrylate, hydroxypropyl(meth)acrylate; (meth) acrylate esters, for example, where the ester group is a polyalkylene oxide or a $C_1$–$C_{30}$ alkoxyl polyalkylene oxide; $C_1$–$C_{30}$ alkyl substituted acrylamides; vinyl sulfonate, acrylamido propane sulfonate; dimethylamino propyl(meth)acrylamide, alkyl vinyl ethers, vinyl chloride, vinylidene chloride, N-vinyl pyrollidone, allyl containing monomers, sulfonates; aromatic vinyl compounds such as styrene, substituted styrenes; butadiene; acrylonitrile; monomers containing aceto acetoxy functional groups such as aceto acetoxy ethyl methacrylate; vinyl esters of saturated carboxylic, e.g. acetate, propionate, neodecanoate; acid or base containing monomers such as, for example, (meth)acrylic acid, itaconic acid, maleic acid, fumaric acid, N,N-dimethylamino ethyl methacrylate; or ii) a polymer with a high acid content, for example, a polymer with from 10 to 60% by weight of the polymer of for example, (meth)acrylic acid, preferably from 10 to 50% methacrylic acid and with a Tg in the range from −30 to >100° C. In some cases, this can give a relatively soft outer phase and is not strictly thought of as a "shell". Suitable outer phase polymers of this type are described in EP 0 576 128 A; and U.S. Pat. No. 4,916,171.

iii) polyvinyl alcohol. This alcohol when used as an outer layer is found to stabilize various copolymers with Tg's in the range from −20 to +95° C., for example, vinyl acetate homopolymer; vinyl acetate/ethylene copolymer; vinyl acetate/ethylene/acrylic acid or ester copolymer; vinyl acetate/acrylic acid or ester copolymer such as but not limited to those disclosed in U.S. Pat. Nos. 4,921,898 and 3,827,996.

The emulsion polymer has an average particle diameter from 20 to 1000 nanometers, preferably from 70 to 300 nanometers. Particle sizes herein are those determined using a Brookhaven Model BI-90 particle sizer manufactured by Brookhaven Instruments Corporation, Holtsville N.Y., reported as "effective diameter". Also contemplated are multi-modal particle size emulsion polymers wherein two or more distinct particle sizes or very broad distributions are provided as is taught in U.S. Pat. Nos. 5,340,858; 5,350,787; 5,352,720; 4,539,361; and 4,456,726.

As used herein, the term "sequentially emulsion polymerized" or "sequentially emulsion produced" refers to polymers (including homopolymers and copolymers) which are prepared in aqueous medium by an emulsion polymerization process in the presence of the dispersed polymer particles of a previously formed emulsion polymer such that the previously formed emulsion polymers are increased in size by deposition thereon of emulsion polymerized product of one or more successive monomer charges introduced into the medium containing the dispersed particles of the pre-formed emulsion polymer.

In the sequential emulsion polymerization of the multi-stage emulsion polymer, the term "seed" polymer is used to refer to an aqueous emulsion polymer dispersion which may be the initially-formed dispersion, that is, the product of a single stage of emulsion polymerization or it may be the emulsion polymer dispersion obtained at the end of any subsequent stage except the final stage of the sequential polymerization.

The glass transition temperature ("Tg") of the emulsion polymer is typically from −60° C. to 100° C., preferably from −20 C. to 50° C., the monomers and amounts of the monomers selected to achieve the desired polymer Tg range are well known in the art. Tgs used herein are those calculated by using the Fox equation (T. G. Fox, Bull. Am. Physics Soc., Volume 1, Issue No. 3, page 123(1956)). that is, for calculating the Tg of a copolymer of monomers M1 and M2, $$1/Tg(\text{calc.}) = w(M1)/Tg(M1) + w(M2)/Tg(M2)$$

wherein

Tg(calc.) is the glass transition temperature calculated for the copolymer w(M1) is the weight fraction of monomer M1 in the copolymer w(M2) is the weight fraction of monomer M2 in the copolymer Tg(M1) is the glass transition temperature of the homopolymer of M1

Tg(M2) is the glass transition temperature of the homopolymer of M2, all temperatures being in °K.

The glass transition temperatures of homopolymers may be found, for example, in "Polymer Handbook", edited by J. Brandrup and E. H. Immergut, Interscience Publishers.

By "active ingredient" we mean any material which promotes utility and function of a pellet containing such an active ingredient in a particular application or process. The active ingredient may include for example, a material which has activity as a pharmaceutical, an agrochemical, a water treatment agent, a water softening agent, a fabric softening agent, a laundry detergent, a hard surface cleaner, a surface polishing agent, a polish stripping material, a biocide, a stone washing agent or a drain pipe cleaner.

It is believed that the pellet aid alone or in co-granulated form creates an adhesive bond between the active ingredient granules within the pellet composition under the conditions of tablet manufacture, which helps to maintain the integrity of the pellet from the point of manufacture, through storage, until used by the customer.

One embodiment of the present invention is pellets which, in addition to the multifunctional pellet aid, contain active ingredients which have activity as a laundry or dish-washing detergent and/or a hard surface cleaner, referred to collectively as detergent-active compounds. The total amount of additive may be from 0.1 to 25% by weight of the pellet, preferably from 0.5 to 15% and most preferably from 0.5 to 5% by weight of the pellet. Such pellets will typically also contain one or more other ingredients which include builders, suitably in an amount of from 5 to 80 wt %, preferably from 20 to 80 wt %; bleaching agents; processing additives; adjuvants; enzymes; scale inhibitors; emulsifiers; surfactants; soaps; dispersants; zeolites; de-greasing agents; anti-foaming agents; phosphates; phosphonates; optical brighteners; fillers; extenders; soil removers; deflocculating agents; anti-coagulants; anti-drift agents; disintegration agents, including for example, water swellable polymers; water-absorbent polymers; water entraining agents, such as, cellulose; plasticizers or coalescing agents, for example, alkylene glycol alkyl ethers, aromatic glycol ethers, alkyl polyglucosides, polysiloxanes, alcohols and alkyl ester acetates; diluents and carriers. Some of the above-mentioned ingredients may also be applicable for use in non-detergent embodiments of pellets.

The pellet aid is incorporated within the body of the pellets of the invention by any suitable method. A preferred method consists of mixing together a dry mixture of the pellet ingredients including one or more pellet aids and then compacting the mixture in a pelletizing machine to form pellets.

Typical compaction loads for commercial pellets without the binders of the present invention can be up to 5000 pounds. The additives of the present invention allow the same pellet formulation to be formed using lower compaction loads. The actual compaction load required will vary depending on the size of the particles, and the composition of the ingredients that constitute the pellet.

It is known from the disclosure of U.S. Pat. No. 5,360,567 that tablets coated with a polymeric binder, namely polyethylene glycol, are also capable of acting as a disintegrant by disrupting the structure of the tablet when the tablet is immersed in water. The prior art of record further teaches that it is highly advantageous for the binder/disintegrant to coat or envelop the detergent matrix particles rather than to be simply mixed with them. The inventors have discovered, surprisingly, that by intentionally preparing a granulated, polymeric pellet aid having granules particle sizes comparable to the active ingredients and fillers that make up a pellet afford a simple and more efficient approach and yields a composition of significant utility.

Granulation is the process of enlarging the size of a particulate composition, whereby small particles are gathered together into larger, permanent, particular aggregates to render them into free-flow particles. The granulation of the pellet aid, as usefully employed in accordance with the present invention, offers the advantages of a) rendering the pellet aid free flowing; b) densifying the pellet aid; c) reducing the problem of dusting of the pellet aid; and more importantly, d) allowing a process for the manufacture of multifunctional pellet aids.

In a second aspect of the present invention, there is provided a process for preparing a multifunctional pellet aid composition including the steps of premixing 0 to 40 % by weight of one or more inorganic solids and 10 to 40% by weight of one or more organic solids, spraying 20 to 80% by weight of one or more solution, suspension or emulsion polymers having a Tg ranging from −20° C. to +95° C. on to the premixed solids to achieve a particle size ranging from 100 $\mu$m to 3000 $\mu$m.

In one embodiment of the process, it is preferred that inorganic solid is a zeolite or equivalent material, the polymeric material is a copolymer of EHA/MAA or an equivalent solution, suspension or emulsion polymer, and the organic solid is a saccharide such as dextrose. The relative amounts of each respective component, as expressed a weight percent, are preferably 20 to 30%: 20 to 50%: 30 to 50%; more preferably 20:40:40. The preferred particle size of the granulated mixture of components that constitutes the pellet aid ranges from 100 $\mu$m to 3000 $\mu$m. A more preferred range of particle size that affords higher binding efficiency is from 200 $\mu$m to 800 $\mu$m. The most preferred particle size of pellet aid granules ranges from 200 $\mu$m to 600 $\mu$m.

In a third aspect of the present invention, there is provided a process for preparing a multifunctional pellet aid composition including the steps of preparing a slurry of 0 to 40 % by weight of one or more inorganic solids and 20 to 80% by weight of one or more solution, suspension or emulsion polymers having a Tg ranging from −20° C. to +95° C. and spraying the slurry on to 10 to 80% by weight of one or more organic solids to achieve a particle size ranging from 100 $\mu$m to 3000 $\mu$m.

In another embodiment of the process, it is preferred that inorganic solid is a zeolite or equivalent material, the polymeric material is a copolymer of EHA/MAA or an equivalent emulsion polymer, and the organic solid is a saccharide such as dextrose. The relative amounts of each respective component, as expressed a weight percent, are preferably 20 to 30%: 20 to 50%: 30 to 50%; more preferably 20:40:40. The preferred particle size of the granulated mixture of components that constitutes the pellet aid ranges from 100 $\mu$m to 3000 $\mu$m. A more preferred range of particle size that affords higher binding efficiency is from 200 $\mu$m to 800 $\mu$m. The most preferred particle size of pellet aid granules ranges from 200 $\mu$m to 600 $\mu$m.

With respect to the second and third aspects of the invention, in an embodiment related to a manufacturing process, granulated pellet aids with higher binding efficiency are scaled up in a fluidized bed granulation process. The underling principles involved in fluidized beds is the turbulent flow or vortex flow suspension of the solid particles in air. The air lifts and separates the powdered ingredients that constitute the pellet aid. The fluidized bed granulation process combines dry mixing, wet granulation and drying. In order to accommodate liquids or slurries in the granulation process, a spray nozzle is mounted somewhere above the rising fluidized bed of powdered ingredients. Through the nozzle system, a liquid or slurry is added to the fluidized powder to achieve granulation and the desired particle size of the pellet aid granules. It is preferred that the pellet aid granules have a particle size ranging from 100 $\mu$m to 3000 $\mu$m. A more preferred range of particle size that affords higher binding efficiency is from 200 $\mu$m to 800 $\mu$m. The most preferred particle size of pellet aid granules ranges from 200 $\mu$m to 600 $\mu$m.

In a separate embodiment, related to the first three aspects of the present invention, a pellet aid composition is prepared from one or more solution, suspension or emulsion polymers and contains no inorganic solids or organic solids. The polymeric pellet aids may be prepared by freeze-drying or spray-drying. A larger amount, 1 to 2% by weight more, of polymeric pellet aid must be used in making pellets as compared to the granulated, polymeric pellet aid used in making pellets.

In a fourth aspect of the present invention, there is provided a process for preparing a solid pellet having high mechanical strength, which can withstand storage and handling without fracturing, and which rapidly disintegrates upon contact with an aqueous system including the steps of mixing 90 to 99.75% by weight of a plurality of ingredients and 0.25 to 10% by weight of a multifunctional pellet aid, wherein the pellet aid comprises (i) 20 to 80% by weight of one or more binders, wherein at least one binder is a solution, suspension or emulsion polymer having a Tg ranging from −20° C. to +95° C.; (ii) 0 to 40% by weight of one or more inorganic solids; and (iii) 10 to 40% by weight of one or more organic solids, the particle size of pellet aid ranging from 100 $\mu$m to 3000 $\mu$m; and compacting the mixture of ingredients and pellet aid to form a pellet.

In one embodiment of this process, it is preferred that plurality of ingredients are used to make a detergent. Typical ingredients that make a detergent can be found in U.S. Pat. Nos. 5,883,061 and 5,360,567, the contents of which is usefully employed in the present invention. The pellet aid is a composition which includes a zeolite or equivalent material, a copolymer of EHA/MAA or an equivalent emulsion polymer, and a saccharide such as dextrose. The relative amounts of each respective component, as expressed a weight percent, are preferably 20:40:40. The amount of pellet aid based on the total weight of ingredients that make up the pellet ranges from 0.25 to 5% by weight, more preferably from 0.5 to 3% and most preferably from 1 to 3%. It is preferred that the pellet aid granules have a particle size ranging from 100 μm to 3000 μm. A more preferred range of particle size that affords higher binding efficiency is from 200 μm to 800 μm. The most preferred particle size of pellet aid granules ranges from 200 μm to 600 μm.

The following examples are presented to illustrate the invention and the results obtained by the test procedures.

Determination of Mechanical Strength of Pellets (Diametal Fracture Stress)

Diametral stress fracture, that is, the amount of force applied to the pellet per unit area (KiloPascals, kPa) at the point the pellet fractures, was determined by slowly applying a continuously increasing load to a pellet of known diameter and thickness, until compression failure (fracture). The diametrical fracture stress, X, was calculated according to the equation:

$$X = 2L/d\, h\pi$$

where L=applied load at point of fracture, d=pellet diameter and h=pellet thickness.

Determination of Pellet Friability

Pellet friability was measured using a friability test device that consisted of a thick glass cylinder, 15 cm in diameter, having three equally spaced glass indentations approximately 2 cm in height. Pellets were placed into the device and tumbled under at a fixed speed. Friability was measured in units of seconds required for the pellet to fracture.

Assessment of the Speed of Disintegration of the Pellets in Water

Each pellet (8 g or 40 g) was placed in a metal wire holder and held at the center of a beaker. Four liters of ambient temperature (20–25° C.) tap water (150 ppm hardness) was added to the beaker. The water was unstirred (i.e. static) and the time taken for the pellet to disintegrate completely out of the holder was determined.

Preparation of Pellets with Pellet Aids of the Present Invention Incorporated Therein as Binder Materials

Direct Compaction of Detergent Pellets Using Pellet Aid as a Dry Binder

Dried, polymeric pellets aids at various weight percentages (as indicated in the Tables below) were mixed thoroughly with generic detergent granules and placed inside a stainless steel cylinder (2.8 cm diameter). A piston rod was inserted into the cylinder and the assembly placed between lower and upper plates of a Carver laboratory pellet press. A specified load stress was applied to the pellet at ambient temperature and the pellet was removed from the cylinder. A range of compacting pressures were used and the diametrical fracture stress, friability and pellet disintegration time (determined as described above) were summarized in the Tables below.

EXAMPLES 1–4

Freeze dried emulsion polymers 1–4 were employed as pellet aid compositions for preparing pellets, as summarized in Table I.

TABLE I

Polymeric Aids for Pellets: Freeze Dried Polymer Additives (at 3% by weight use levels based on total pellet weight)

| Sample | Compositions | Tg (° C.) | Morphology | Hardness (kPa) | Friability (sec) |
|---|---|---|---|---|---|
| 1 | 30 MAA/70 EHA | 1 | Fibrous | 9.31 | 34 |
| 2 | 53EA/19MMA/10H EMA/18MAA | 53 | Flake Powder | 24.87 11.09 | 360 12 |
| 3 | 32EA/40MMA/10H EMA/18MAA | 89 | Flake powder | 15.49 9.49 | 36 8 |
| 4 | 25BA/47MMA/10H EMA/18MAA | 95 | Flake Powder | NA 7.71 | 54 4 |

Key
EA = ethyl acrylate
BA = butyl acrylate
MMA = methyl methacrylate
MAA = methacrylic acid
EHA = 2-ethyl hexyl methacrylate
HEMA = hydroxy ethyl methacrylate Table I summarizes polymers synthesized from various combinations of monomers in freeze dried form which exhibit high binding efficiency as aids for detergent tablets using direct compression. The pellets contained 3 wt % of a specific polymeric pelleting aid composition. The performance of a specific polymeric pellet aid appears to be directly related to the morphology of the polymer that makes up the pellet aid composition. The binding efficiency of pellet aids exhibiting a "flake" type morphology is considerately higher than the same pellet aids exhibiting a "fine powder" morphology.

The emulsion copolymers summarized in Table I exhibited a broad glass transition temperature, from 1° C. to 95° C. A useful range of Tg for the purposes of the present invention ranges from –20° C. to 95° C. All pellets prepared from the polymeric pellet aids exhibited similar mechanical strengths, as determined from friability tests. Morphological differences in the pellet aids appear to have the greatest influence on the mechanical strength of the resulting pellets.

EXAMPLES 5–7

Examples 5–7 are spray-dried EHA/MAA co-polymers having a range of particle sizes that are used to prepare pellet aids, as summarized in Table II.

TABLE II

Spray Dried Polymeric Pellet Aids

| Sample (EHA/MAA) | Friability (sec) at Compaction Load (lb)* | | | Particle Size (μm) | Bulk Density (g/ml) |
|---|---|---|---|---|---|
| | 250 lb | 500 lb | 1000 lb | | |
| Control (no EHA/MAA) | 5 | 13 | 27 | NA | NA |
| 5 | 67 | 179 | 297 | 40 | 0.309 |
| 6 | 8 | 8 | 80 | 100 | 0.36 |
| 7 | 23 | 96 | 145 | 100 | 0.29 |

*(at 3% by weight use levels based on total pellet weight)

Table II summarizes the performance data for spray-dried polymeric pellet aids. The samples in Table II possess the same polymer compositions, but exhibit different physical properties, such as particle sizes and bulk density. Sample 5 has a smaller particle size (40 μm) and exhibits the highest binding efficiency in terms of friability and a concomitant improvement in mechanical strength in the resulting pellet. Samples 6 and 7 possess the same particle size (100 μm), but different bulk densities. Sample 7 exhibits higher binding efficiency and higher mechanical strength in the resulting pellet. It appears that the binding efficiency of a specific pellet aid strongly correlates with its bulk density. The less the bulk density, the higher the binding efficiency. Microscopic analysis demonstrates that a majority of the polymer particles that constitute the pellet aid exhibited "balloon" or "hollow" type structures/morphologies. Under tablet compaction conditions, the hollow structures collapse into smaller particles, thereby increasing their surface area. The effect of adding such a pellet aid provides a more robust pellet with improved mechanical strength. As the bulk density decreases for a given polymeric pellet aid, the percentage of the "balloon" structure increases, therefore, its binding efficiency increases as does the mechanical strength of the resulting pellet, as shown in Table II for Examples 6 and 7.

EXAMPLES A–O

Examples A–O are granulated polymeric pellet aids used to prepare pellets, as summarized in Tables III and IV.

In Examples A–O, polymeric co-granules were prepared by granulating various polymer emulsions with some inorganic and organic solids, such as zeolite, soda ash, synthetic $SiO_2$, dextrose and starches. The granulates were prepared in a Kitchen Aid apparatus and dried in a fluidized bed apparatus at 50° C. The binding efficiency of the resulting granules were tested and the results are summarized in Table III and IV.

TABLE III

Examples of Co-granulated Polymeric Pellet Aids

| Example | Solid 1 (PS, μm) | Amount added | Emulsion/ Solid 2 | Amount added | Filter | Comments | Friability (sec) 250 lb load* |
|---|---|---|---|---|---|---|---|
| A | Spray Dried Sample 1 powder (20 μm) | 20 gm | Sample 1 | 10 gm | yes | clumps after filtration | 5 sec |
| B | Zeolex 7A | 20 gm | Sample 1 | 10 gm | yes | free flowing powder | 3 sec |
| C | Zeolex 7A | 20 gm | Sample 1 | 20 gm | yes | free flowing powder | 3 sec |
| D | Pregel Corn Starch | 40 gm | Sample 1 | 30 gm | no | Requires breaking w/Waring blender free flowing powder | 1000 lb load 56 sec |
| E | Spray Dried Sample 1 (100 μm) | 20 gm | Zeolite + Sample 1 | 5 gm 10 gm | yes | free flowing powder | 12 sec |
| F | Spray Dried Sample 1 (20 μm) | 20 gm | Na Carb + Sample 1 | 5 gm 5 gm | yes | free flowing powder | 8 sec |
| G | Spray Dried Sample 1 (100 μm) | 20 gm | Na Carb + Sample 1 | 5 gm 5 gm | yes | free flowing powder | 3 sec |
| H | Spray Dried Sample 1 (20 μm) | 20 gm | Na Carb + Sample 1 | 10 gm 5 gm | yes | free flowing powder | 12 sec (1000 lb) 30 sec |
| I | Spray Dried Sample 3 | 20 gm | Hubers or 600 + Sample 3 | 5 gm 25 gm | yes | Granulated, then Fluidized bed dried 50° C. for 20 mins | 19 sec 24 sec |
| J | Spray Dried Sample 3 | 20 gm | Zeolex 7A + Sample 3 | 5 gm 35 gm | yes | Granulated, then Fluidized bed dried 50° C. for 20 mins | 37 sec |

Key:
Zeolex 7A = Zeolite,
Na Carb = Sodium Carbonate,
Hubersorb 600 = Synthetic $SiO_2$
Pregel Corn Starch = Pregelatinized corn starch
*(at 3% by weight use levels based on total pellet weight)

TABLE IV

Examples of Co-granulated Polymeric Pellet Aids

| Example | Solid 1 | Amount added | Emulsion/ Solid 2 | Amount added | Particle Size Range ($\mu$) | Friability* @ 1000 psi (sec) |
|---|---|---|---|---|---|---|
| K | Camdex | 20.06 g | Zeolex 7A + Sample 1 | 10 g 18.17 g | 150–250 | 80 |
| L | Camdex | 5 g | Zeolex 7A + Sample 1 | 15.1 g 23.27 g | 150–355 | 49 |
| M | Tapioca Starch | 5.05 g | Zeolex 7A + Sample 1 | 15.08 g 26.29 g | 150–355 | 42 |
| N | Stadex 125 | 5.01 g | Zeolex 7A + Sample 1 | 15 g 31.95 g | 150–355 | 55 |
| 0 | Pure-Dent B810 | 5.02 g | Zeolex 7A + Sample 1 | 15 g 26 g | 355–1400 | 52 |

*(at 6% by weight use levels based on total pellet weight)
Key:
Camdex = dexstrates (95% dextrose, 5% starch)
Stadex 125 = Dextrin
Pure-Dent B810 = Corn Starch The granulation process is usefully and preferably employed in accordance with the invention for the manufacture of multifunctional, polymeric pellet aids having improved flow properties and reduce dusting behavior. Table III demonstrates that a variety of inorganic and organic solids can be used to formulate pellet aids via the granulation process. The resulting co-granulated pellet aids exhibit high binding efficiencies for the ingredients that make up a pellet. A polymeric disintegrating agent and a wicking agent can also be combined with the polymeric binder to produce a multifunctional pellet aid. Suitable disintegrating agents include for example super absorbent polymers, such as for example cross-linked polyacrylic acid and equivalent materials. Organic solids such as for example dextrose, cellulose derivatives and equivalent materials are good wicking agents, which can facilitate the transport of water by physically entraining water into the center of the pellets, the co-granulated pellet aids can also accelerate the disintegration time of the tablets. Co-granulated pellet aids and the processes used to formulate them, therefore, substantially reduce the production costs as compared to dry polymeric pellet aids in the absence of co-granulated inorganic and organic solids, as well as providing pellet aid having multifunctional properties (e.g. binder, disintegrating agent, wicking agent, whitening agent, etc.), as shown in Tables V and VI.

TABLE V

Performance Data for Pellets Using Co-granulated Pellet Aids

| Tablet (40 gram) | Compaction Load (lb) | Dwell Time (second) | Disintegration Time (min:sec) | Friability (min:sec) |
|---|---|---|---|---|
| 1% Disintegrant | 500 | 15 | >6 min | |
| 1% Disintegrant + 2% K | 500 | 15 | 3:20 | 0:59 |
| 1% Disintegrant + 4% K | 500 | 15 | 2:40 | 1:53 |

Disintegrant = cross-linked poly(meth)acrylic acid

The data in Table V shows that co-granulated pellet aid K of the present invention improved both the mechanical strength and disintegration rate of the resulting pellets, as measured by friability testing and disintegration time, respectively. The data demonstrates that the co-granulated pellet aid can function as a binder (increases the mechanical strength of the resulting pellets), and a disintegration agent (improves the disintegration rate of the resulting pellets).

TABLE VI

Performance Data for Detergent Pellets Using Co-granulated Pellet Aids
Generic Powder Detergent-Antiredeposition Test

| | X | Y | Z | Whiteness Index (WI) | ΔWI |
|---|---|---|---|---|---|
| Cotton 405 | | | | | |
| No Polymer (CONTROL) | 78.07 | 81.57 | 75.53 | 35.5 | |
| 0.5% Acusol 445N* | 79.99 | 84.11 | 82.08 | 52.88 | 17.38 |
| 0.5% Spray Dried (SD) Sample 1 | 77 | 80.51 | 75.1 | 37.11 | 1.61 |
| 0.5% A445N / 0.5% SD Sample 1 | 81.4 | 85.52 | 82.98 | 51.88 | 16.38 |
| 1.0% A445N | 82.35 | 86.73 | 86.25 | 60.75 | 25.25 |
| 1.0% K | 80.04 | 84.03 | 80.62 | 47.49 | 11.99 |
| PE/Cotton | | | | | |
| No Polymer | 68.15 | 70.58 | 62.76 | 20.4 | |
| 0.5% Acusol 445N | 74.99 | 79.19 | 78.12 | 53.33 | 32.93 |
| 0.5% Spray Dried (SD) Sample-1 | 67.14 | 69.91 | 62.73 | 22.6 | 2.2 |
| 0.5% A445N / 0.5% SD Sample-1 | 77.61 | 82.07 | 82.43 | 60.95 | 40.55 |
| 1.0% A445N | 79.59 | 84.41 | 87.87 | 74.8 | 54.4 |
| 1.0% K | 76.9 | 81.38 | 81.92 | 61.2 | 40.8 |

*A445N is polyacrylic acid, a popular polymer dispersant used a variety of detergent formulations for antiredeposition of Calcium onto fabric.

Antiredeposition Test was performed using a standard Terg-O-Tometer. In each wash bath, 2 cotton 405 cloths and 2 polyester/cotton cloths were added into 1000 ml wash solution with 5 ml oily soil load. 0.15% Generic Powder Detergent and 0.5% or 1.0% Polymeric Pellet Aid were added in wash bath with wash water at 35° C., the hardness of the wash water was 300 ppm. Three wash cycle and three rinse cycle were used, each wash cycle was 12 minutes and each rinse cycle was 3 minutes. The whiteness index (WI) of the washed cloths were examined after the cloths were dry.

The results in Table VI indicate that a significant increase in whiteness index is obtained with the polymeric pellet aids of the present invention. The data demonstrates that the polymeric pellet aids of the present invention can function as dispersant in generic detergent formulations.

We claim:

1. A multifunctional pellet aid comprising:
   (a) 20 to 80% by weight of one or more acrylic based polymers having a Tg ranging from −20° C. to +95° C.;
   (b) 0 to 40% by weight of one or more inorganic solids; and
   (c) 10 to 80% by weight of one or more organic solids, wherein the particle size of the pellet aid ranges from 100 μm to 3000 μm, wherein 0.25 to 10% by weight of the pellet aid is added to a plurality of ingredients and compacted to form a pellet and wherein the pellet aid functions as a binder, a disintegration agent, a wicking agent and combinations thereof.

2. The multifunctional pellet aid according to claim 1, wherein the ingredients of the pellet aid are selected from the group consisting of acrylic based solution polymers, acrylic based suspension polymers, acrylic based emulsion polymers, saccharides, dextrose, glucose, sucrose, maltose, fructose, cyclodextrins, cyclodextrin derivatives, polysaccharides, starch, starch derivatives, cellulose, cellulose derivatives, carboxymethylcellulose, cellulose ethers, methyl cellulose, ethyl hydroxyethyl cellulose, cross-linked cellulose derivatives, naturally occuring gums, tragacanth gum, gum arabic and combinations thereof; wherein the inorganic solids are selected from the group consisting of zeolites, clays, alkali metal silicates, alkaline-earth metal silicates, silica, alkali metal carbonates, alkaline-earth metal carbonates, alkali metal citrates and alkaline-earth metal citrates, alkali metal acetates, alkaline- earth metal acetates and combinations thereof; and wherein the organic solids are selected from the group consisting of poly(meth)acrylic, saccharides, dextrose, glucose, sucrose, maltose, fructose, cyclodextrins, cyclodextrin derivatives, polysaccharides, starch, starch derivatives, cellulose, cellulose derivatives, sodium carboxymethylcellulose, cellulose ethers, methyl cellulose, ethyl hydroxyethyl cellulose, cross-linked cellulose derivatives and combinations thereof.

3. The multifunctional pellet aid according to claim 1, wherein one or more acrylic based polymeric binders and one or more organic solids are co-granulated.

4. The multifunctional pellet aid according to claim 1, wherein one or more polymeric binders, one or more inorganic solids and one or more organic solids are co-granulated.

5. The multifunctional pellet aid according to claim 1, wherein acrylic based polymeric binders are prepared from one or more monomers selected from the group consisting of (meth)acrylic acid, (meth)acrylate esters, $C_1$–$C_{30}$ alkyl substituted acrylamides, vinyl sulfonate, acrylamido propane sulfonate; dimethyl amino propyl acrylamide, alkyl vinyl esthers, vinyl chloride, vinylidene chloride, N-vinyl pyrollidone, allyl containing monomers, an aromatic vinyl compounds, a substituted aromatic vinyl compound, butadiene, acrylonitrile, ethylenically unsaturated monomers containing aceto acetoxy functional groups, vinyl esters of saturated carboxylic acids and combinations thereof.

6. The multifunctional pellet aid according to claim 1, wherein the acrylic based polymers are selected from the group consisting of:
   i) a multiphase polymer having at least one inner phase polymer with a Tg in the range from −85 to +35° C. and at least one outer phase polymer with a Tg in the range from +40 to +160° C.; or
   ii) a multiphase polymer having a inner phase which comprises a polymer with a Tg in the range from −85 to +35° C. and outer phase with a carboxylic acid content 10 to 60% by weight of the multiphase polymer wherein the outer phase has a Tg in the range from −30 to >100° C., and combinations thereof; or
   a copolymer having a Tg in the range from −85 to +35° C. which is stabilized with polyvinyl alcohol.

7. The multifunctional pellet aid according to claim 6, wherein the multiphase polymer is prepared by emulsion polymerization.

8. A pellet composition comprising one or more active ingredients and one or more pellet aids, wherein the pellet aid comprises
   (i) 20 to 80% by weight of one or more acrylic based polymeric binders having a Tg ranging from −20° C. to +95° C.;
   (ii) 0 to 40% by weight of one or more inorganic solids; and
   (iii) 10 to 40% by weight of one or more organic solids; and
   wherein the pellet aid is present in the pellet in an amount from 0.25 to 10% by weight and has a particle size ranging from 100 μm to 3000 μm, wherein 0.25 to 10% by weight of the pellet aid is added to a plurality of ingredients and compacted to form a pellet and wherein the pellet aid functions as a binder, a disintegration agent, a wicking agent and combinations thereof.

9. A pellet composition according to claim 8, wherein the active ingredient is a material having activity as a pharmaceutical, an agrochemical, a water treatment agent, a water softening agent, a fabric softening agent, a laundry detergent, a hard surface cleaner, a surface polishing agent, a polish stripping material, a biocide, a stone washing agent a drain pipe cleaner and combinations thereof.

10. A process for preparing a multifunctional pellet aid which comprises the steps of:
   (a) premixing 0 to 40% by weight of one or more inorganic solids and 10 to 40% by weight of one or more organic solids; and
   (b) spraying 20 to 80% by weight of one or more acrylic based emulsion polymers having a Tg ranging from −20° C. to +95° C. on to the premixed solids to achieve a particle size ranging from 100 μm to 3000 μm.

11. A process for preparing a multifunctional pellet aid which comprises the steps of:
   (a) preparing a slurry of 0 to 40% by weight of one or more inorganic solids and 20 to 80% by weight of one or more acrylic based emulsion polymers having a Tg ranging from −20° C. to +95° C.; and
   (b) spraying the slurry on to 10 to 40% by weight of one or more organic solids to achieve a particle size ranging from 100 μm to 3000 μm.

12. The process according to claim 10, wherein the particle size of the granulated mixture of binders, inorganic solids and organic solids that constitutes the pellet aid ranges from 200 μm to 800 μm.

13. The process according to claim 11, wherein the particle size of the granulated mixture of binders, inorganic solids and organic solids that constitutes the pellet aid ranges from 200 μm to 800 μm.

14. The process according to claim 13, wherein the particle size of the pellet aid granules exhibiting higher binding efficiency ranges from 200 μm to 600 μm.

15. A process for preparing a solid pellet having high mechanical strength, which can withstand storage and handling without fracturing, and which rapidly disintegrates upon contact with an aqueous system comprising the steps of:
  (a) mixing 90 to 99.75% by weight of a plurality of ingredients and 0.25 to 10% by weight of a multifunctional pellet aid,
wherein the pellet aid comprises
    (i) 20 to 80% by weight of one or more acrylic based polymers having a Tg ranging from −20° C. to +95° C.;
    (ii) 0 to 40% by weight of one or more inorganic solids; and
    (iii) 10 to 40% by weight of one or more organic solids, the particle size of pellet aid ranging from 100 μm to 3000 μm, wherein the pellet aid functions as a binder, a disintegration agent, a wicking agent and combinations thereof; and
  (b) compacting the mixture of ingredients and pellet aid to form a pellet.

16. The multifunctional pellet aid according to claim 2, wherein one or more acrylic based polymeric binders and one or more organic solids are co-granulated.

17. The multifunctional pellet aid according to claim 2, wherein one or more polymeric binders, one or more inorganic solids and organic solids are co-granulated.

18. The process according to claim 10, wherein the pellet aid functions as a binder, a disintegration agent, a wicking agent and combinations thereof.

19. The process according to claim 11, wherein the pellet aid functions as a binder, a disintegration agent, a wicking agent and combinations thereof.

20. The pellet composition according to claim 8, wherein the range of particle sizes of the pellet aid matches the range of particles sized of the remaining ingredients the resulting pellet granules have particle sizes greater than the initial particle sizes of the pellet aids and ingredients.

* * * * *